Figure 1:
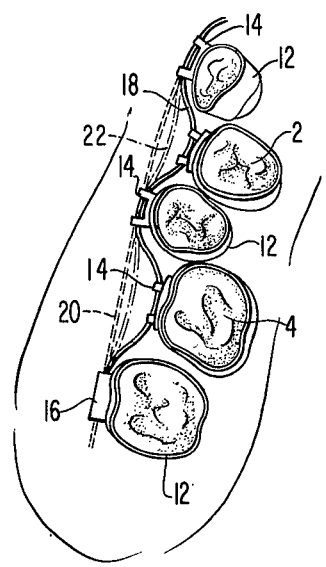

United States Patent [19]
Andreasen

[11] 4,037,324
[45] July 26, 1977

[54] METHOD AND SYSTEM FOR ORTHODONTIC MOVING OF TEETH

[75] Inventor: George F. Andreasen, Iowa City, Iowa

[73] Assignee: The University of Iowa Research Foundation, Iowa City, Iowa

[21] Appl. No.: 362,578

[22] Filed: May 21, 1973

Related U.S. Application Data

[63] Continuation-in-part of Ser. No. 259,184, June 2, 1972, abandoned.

[51] Int. Cl.$^2$ ............................................. A61G 7/00
[52] U.S. Cl. ................................................... 32/14 A
[58] Field of Search ............................. 32/14 R, 14 A

[56] References Cited

U.S. PATENT DOCUMENTS 3,504,438    4/1970    Wittman et al. .................... 32/14 A

OTHER PUBLICATIONS

"An Evaluation of 55 Cobalt Substituted Nitinol Wire for Use in Orthodontics", *JADA*, vol. 82, June 1971, pp. 1373–1375.

*Primary Examiner*—Robert Peshock
*Attorney, Agent, or Firm*—Beveridge, DeGrandi, Kline & Lunsford

[57] ABSTRACT

Orthodontic movement of malaligned teeth is performed by attaching to the teeth a wire which has properties useful in orthodontics. When the anticipated use of the wire involves torsional and flexural stresses, the wire is a single strand of a material having a higher elastic limit and a lower elastic modulus than an 18-8 stainless steel wire of identical cross-section. The invention also contemplates the use of wires which demonstrate a plastic memory which causes them to return to a preset shape or length after being deformed and then heated. For example, longitudinally shrinkable wires are either attached to teeth for closing the spaces therebetween or are used to draw a tooth toward a fixed reference member such as a rigid archwire spaced from the tooth. The mechanical memory of the wire may also tend to restore it to a preset shape upon heating in order to level or torque malposed teeth. The disclosed wires are formed of Nitinol alloy which is a known near-stoichiometric alloy of nickel and titanium. When the wire exerts tooth-moving forces by being subjected to torsional or flexural stresses, the alloy also includes cobalt substituted for nickel on an atom-for atom basis so that the composition is $TiNi_{.935}Co_{.065}$.

19 Claims, 5 Drawing Figures

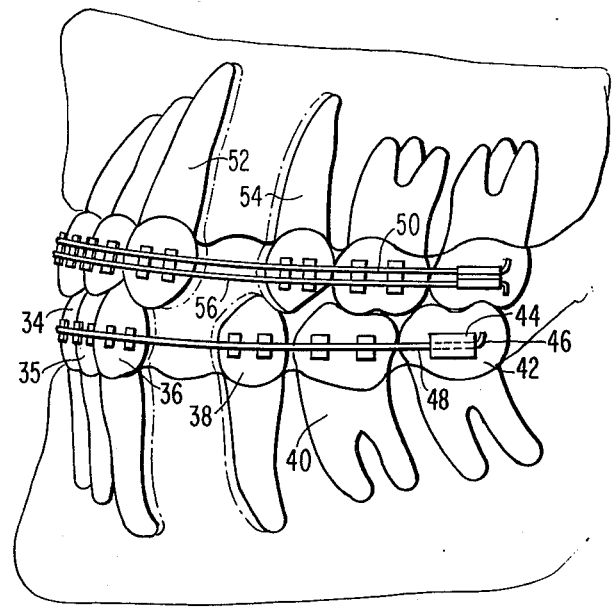
FIG. 3
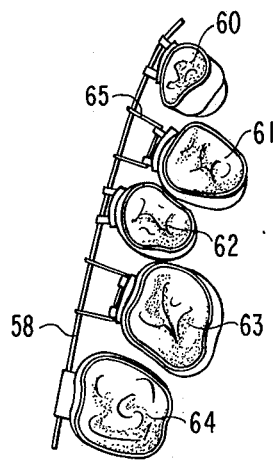
FIG. 4
FIG. 5
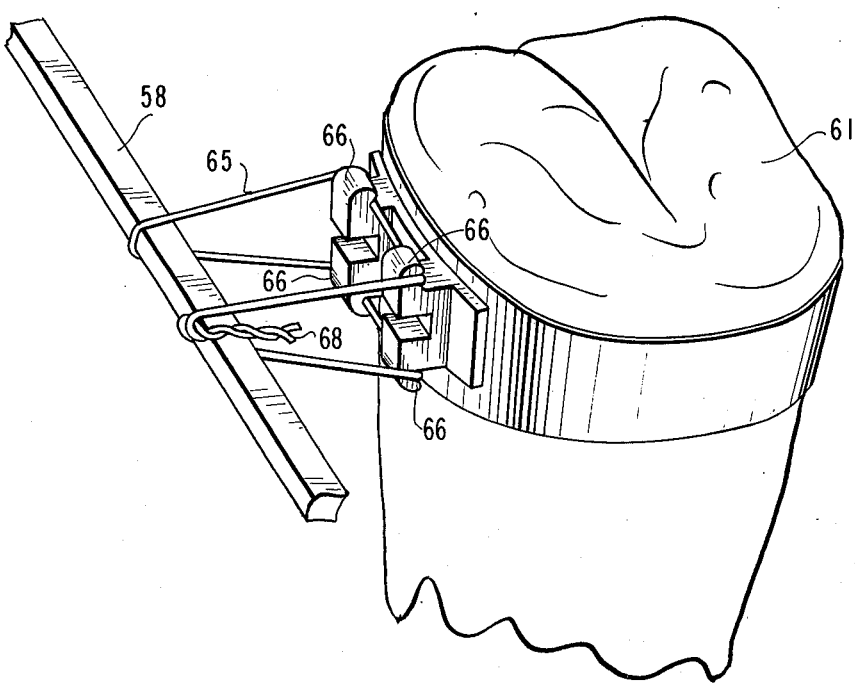

METHOD AND SYSTEM FOR ORTHODONTIC MOVING OF TEETH

This is a Continuation-in-Part of my earlier application Ser. No. 259,184, filed June 2, 1972, and now abandoned, and entitled Method and System for Orthodontic Leveling of Teeth.

This invention pertains to a novel method and system for orthodontic moving of teeth.

Customary orthodontic procedures involve the attachment of brackets to individual teeth by means of bands which encircle the teeth. A resilient wire is attached to the brackets in a manner so that flexural and/or torsional stresses are placed in the wire to create restorative forces tending to bring the teeth toward a desired position. Such techniques, in their broader sense, include the cervical headgear which includes a laterally-biased U-shaped wire which attaches only to the molars, but in most instances it will involve an archwire of parabolic shape which is attached by siamese brackets to most of the teeth in the upper or lower jaw.

Current orthodontic practices for leveling teeth usually call for the sequential use of several archwires, made of 18-8 stainless steel.

It is not practical to commence treatment with the largest size archwire for several reasons. The bracket slots have little semblance of alignment with each other so that the wires must be substantially twisted or deflected. The larger wires such as 0.020 inch diameter 18-8 stainless steel wire undergo permanent deformation more easily than smaller wires, thus impairing their ability to impose moving forces on the teeth after being twisted or deflected significantly. Also, since the teeth move during the period between visits to the orthodontist, the alignment — producing forces are reduced. Spring-like loops have been placed in wires to avoid this problem, but such loops are a source of irritation and often produce ulceration of adjacent body tissue.

To avoid the problems introduced by large wires, it is customary for a typical sequence of treatment to involve first use of a small 0.014 inch diameter archwire for preliminary tooth movement, followed by the use of 0.016 inch or 0.018 inch archwire. The final stage may involve the use of an archwire of rectangular cross-section which fills the slot in the bracket; however, at this stage of treatment the brackets are substantially aligned with each other so that the rectangular wire is not subjected to a large degree of deflection or torsion. The rectangular wire will be twisted slightly between adjacent teeth and its rectangular shape renders it non-rotatable with respect to each bracket and tooth, thereby imposing torquing or uprighting forces on the teeth.

The present invention in one respect contemplates the reduction or elimination of archwire changes, and the improvement in the characteristics of orthodontic devices such as cervical headgear. These objectives are realized by the use of wires made of a metallic composition which is deformable by a martensitic shear mechanism when below a critical temperature and possesses a mechanical memory by returning to its original form when heated above said critical temperature. The wire is alternatively described and claimed as a single strand made of a metallic composition which has a higher elastic limit and a lower modulus of elasticity than an 18-8 stainless steel wire of the same cross-section. The disclosed and preferred composition is known in the art as a Nitinol alloy which is a near-stoichiometric alloy of nickel and titanium, preferably having cobalt substituted for the nickel on an atom-by-atom basis and possessing the composition of about $TiNi_{.935}Co_{.065}$.

Another inventive concept pertains to orthodontic devices which use wires which shrink or contract longitudinally upon being heated.

Existing orthodontic practices sometimes call for the use of spring loops in an archwire or rubber bands for imposing forces on teeth which are to be moved. Rubber band elastics decay and lose their strength rapidly, and must be replaced daily for effective treatment; however, such replacement is dependent upon the patient and experience has shown that many patients do not adhere faithfully to the recommended procedure. In order to avoid the necessity for rubber band replacement and to place control in the hands of the orthodontist, this invention proposes to use a longitudinally shrinkable wire which is attached to the tooth and to a reference member, the latter either being another tooth, a stiff archwire or any other convenient anchoring member. The wire is dimensionally set when installed in the mouth, but is shrinkable in response to subsequent heating either by body temperature or an external heat source. The wire or other elongated member is heated, causing it to shrink longitudinally so that it will be under tension to exert a moving force on the tooth. Two examples of this later concept are disclosed herein. In one case, the wire is used as a ligature wire which draws a tooth-attached bracket toward a stiff archwire, and the other instance the archwire itself is shrinkable to reduce the arch circumference, thereby closing the space between adjacent teeth. The above-discussed Nitinol alloy is suitable for this purpose.

Another aspect of the invention pertains to the use of an elongated member, typically a wire formed of Nitinol alloy, which has a preset shape before being attached to the teeth, is deformed by flexion or torsion for attachment to the teeth, and possesses a mechanical memory which causes it to resume the preset shape when heated. When such a wire is heated after being attached to malposed teeth, the teeth prevent its immediate return to its preset shape, but the forces urging it toward the preset shape are exerted upon the teeth to level or torque them.

The Nitinol alloys are known to have unusual properties in that they are quite ductile when below a critical temperature (known in the literature as transition temperature range or TTR) due to martensitic shear wherein adjacent planes of atoms shift by a distance less than a full interatomic distance. When a body deformed in this manner is heated above its critical temperature (TTR), it displays the characteristic of mechanical memory, returning toward its original or pre-deformation shape. It is believed that strong, energetic and directional electron bonds operate to pull the displaced atoms back to their previous positions. The TTR of this preferred unannealed 0.019 inch diameter wire of $TiNi_{.935}Co_{.065}$ is about 40° F., well below normal body temperature.

Figure 2:
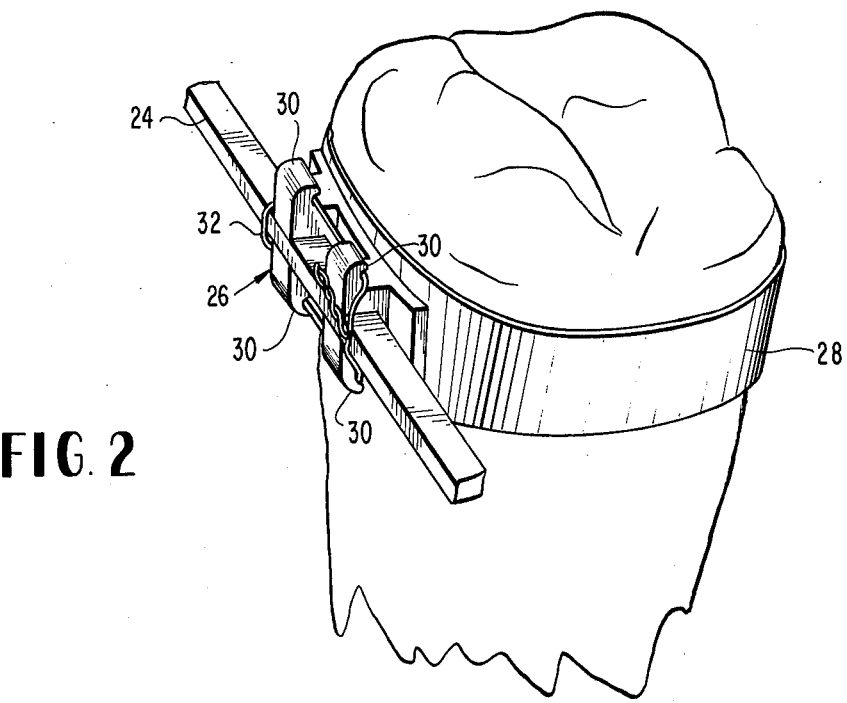

For a more complete understanding of several embodiments of the invention, reference is made to the accompanying drawings wherein FIG. 1 illustrates the use of a round archwire used to level teeth by imposing thereon forces produced by flexural stresses in the archwire;

FIG. 2 is an enlarged view of a single tooth having a standard siamese bracket and ligature wire, said tooth having connected thereto an archwire of rectangular cross-section. The archwire is under torsional stresses so that it will move the root of the tooth in a manner referred to in the art as torquing, uprighting or paralling of the teeth;

FIG. 3 illustrates two ways in which archwires having a mechanical memory may be used to move teeth. On the upper jaw, twin-slotted siamese brackets are used with a shrinkable archwire in the upper set of slots and an unshrinkable second archwire in the lower set of slots, the latter serving to level the teeth toward the ideal arch form and guide the closing movement of teeth produced by the shrinkable archwire. On the lower jaw, a preformed archwire which has a mechanical memory is used to level the teeth, torque the teeth to an upright orientation and close the spaces between the teeth; and, FIGS. 4 and 5 illustrate the use of a shrinkable ligature wire for drawing a displaced tooth toward a stiff archwire. FIG. 4 shows a plurality of teeth to indicate the support means for the archwire and the relative positioning of the teeth. FIG. 5 shows a single banded-and-bracketed tooth and the details of the connection of the shrinkable ligature wire to the stiff archwire.

As will be seen in FIG. 1, the five teeth are malaligned with the first bicuspid 2 and first permanent molar 4 being located a substantial distance inside the next adjacent teeth. Each of the teeth is encircled by a band 12. Conventional siamese brackets 14 are on each band, except that the second permanent molar has a conventional tube 16 for retaining the end of the archwire 18.

Prior to placing the archwire in the mouth, the clinician may either refrigerate the wire to a temperature below the TTR and bend it into the arch shape or he may work it while above the TTR, over-bending it with wire bending pliers in order to attain the preferred initial arch shape and to place the small bends known as "offsets" in the wire. These steps may be avoided if archwires are preformed and set into the desired arch shape at high temperatures by a manufacturer.

The ends of the wire may be annealed to permit the formation of loops for stops in the wire and to permit clinching back of the distal end of the wire. Alternatively, stops may be soldered onto the wire.

The archwire 18 is subjected to flexural stresses by attaching it to each of the brackets 14 and to the tube 16. Due to the resilience of the archwire which tends to restore it to its unstressed position shown in broken lines at 20, it imposes on the brackets and the teeth relative forces which tend to move the teeth into proper alignment, i.e., drawing the first bicuspid 2 and first permanent molar 4 outwardly toward an aligned relationship with the next adjacent teeth.

The archwire is tied into the brackets, using contouring pliers if a preformed arch is not available. Tying is done in a conventional fashion by the use of ligature wires tied into the four slots of each of the archwire receiving ears on the bracket. Preferably, only a single wire is used, and it may be deflected at least 3 millimeters from its unstressed rest position in the course of attaching it to the brackets, which is a distance significantly greater than was permissible with the prior stainless steel archwires. Typical siamese brackets are 0.135 inch wide and spaced apart by an interbracket distance of about 0.200 inch when attached to teeth of average size.

After initial installation of the leveling system, the patient should be seen briefly every three or four weeks, only for a visual check to ensure that the wire has not undergone excessive permanent deformation as a result of forces of mastication. After about three months from the time of initial installation, if the wire has not completely leveled the teeth, it may be removed and another wire of the same composition installed in the brackets. In a typical case, the archwire will be found to have undergone permanent deformation creating slight undulations of about 5 to 8% as a result of creep in the wire and long-term masticating forces.

Prior clinical techniques hve dictated that the wire or wires not be deflected more than two millimeters from their unstressed rest position between adjacent brackets. The reason for this will be understood by referring to the broken line 22 in the drawings which shows the amount of permanent deformation experienced after one hour by a single 18-8 stainless steel wire having a diameter of 0.020 inch. Of course, the use of smaller stainless steel wires in accordance with usual procedure would not produce permanent deformation this great. The wire of the present invention underwent a permanent deformation in one hour substantially less than stainless steel and, in one instance where contouring pliers had not been used, returned to the position 20. When wires according to the invention were attached to the brackets by using contouring pliers, the deformation was somewhat greater, but the wires still returned at least 90% of the distance toward their pre-deformation position. In this same experimentation, an annealed wire of the same alloy was permanently deflected by an amount comparable to a stranded stainless steel wire of approximately the same size, the latter being a conventional archwire sold under the Twistflex trademark.

While the round archwire 18 shown in FIG. 1 utilizes the flexural stresses imposed thereon during installation for the purpose of creating tooth-moving forces, wires of the preferred composition may also be subjected to torsional forces during installation. When non-rotatably affixed to a bracket, a torsionally stressed wire will deliver torsional stresses to the brackets and the attached teeth.

As is well known in orthodontic practice, teeth may be moved by the use of a torsionally-stressed rectangular archwire which completely fills the bracket slots so as to be non-rotatable with respect to the bracket. This procedure is known in the art as "torquing", "uprighting", or "paralleling". The rectangular archwire 24 may have both torsional and flexural stresses so that it will concurrently move the teeth in the manner of the circular archwire illustrated in FIG. 1 and to parallel the teeth according to FIG. 2.

In FIG. 2, a torsion-delivering archwire is designated 24. It has a rectangular cross-section which corresponds to the shape of the slots in the bracket 26. This is a conventional siamese bracket attached to a tooth by an encircling band 28 with spaced-apart pairs of ears 30 for receiving the archwire therebetween. Each of these ears has a recess or slot which faces in the direction of the attached tooth for receiving a ligature wire 32. As indicated in FIG. 2, the ligature wire 32 is passed over the archwire 24, along the slots on each of the ears 30 and then back over the archwire where it is twisted together, with the twisted portion being tucked in to prevent irritation of the adjacent mucous membrane tissues of the patient. The rectangular archwire 24 is twisted about its longitudinal axis between adjacent brackets, thereby torquing the teeth to an upright position.

Most of the preceding discussion has involved the use of archwires, but the invention is capable of other uses such as for the construction of the spring bow which is attached to the molar tubes in a conventional cervical headgear device.

The embodiments of FIGS. 3, 4 and 5 are concerned with the use of wires or other elongated elements which are essentially dimensionally set when placed in the mouth, and then change their dimensions or shape in response to increased temperatures resulting from body heat or an external heat source. Nitinol alloys exhibit this characteristic which is known as mechanical memory. When Nitinol alloys are below their transition temperature range (TTR), they are quite ductile due to martensitic shear where adjacent planes of atoms shift by a distance less than a full interatomic distance. When a body deformed in this manner is heated above its critical temperature (TTR), its mechanical memory returns it toward its original or pre-deformation shape. It is believed that strong, energetic and directional electron bonds operate to pull the displaced atoms back to their previous positions. Such wires may be bent or elongated while below their TTR and then heated so that the memory-created forces urge the wire to its preset unbent or unelongated form to create tooth-aligning forces.

The embodiment of the invention shown in FIG. 3 includes a longitudinally shrinkable archwire which is attached to the teeth by a conventional band-and-bracket system. On the lower jaw, the teeth 34-40 have conventional siamese brackets of the type illustrated in FIG. 2, and the molar 42 has a standard molar tube 44 which retains the bent end 46 of the shrinkable archwire 48. The archwire is preferably a near-stoichiometric alloy of nickel and titanium which, as previously mentioned, is known to possess a mechanical memory when heated to a temperature above a critical temperature known as a transition temperature range (TTR). Preferably, the TTR is above normal room temperature of about 72° F. and below normal body temperature. A TTR of about 80°-90° F. is ideal. Prior to its installation in the mouth, the wire is stretched to increase its length and reduce its cross-section. A typical archwire length may be about 100 mm, and this may be stretched about 10% which will elongate the wire about 7 or 8% until it is reheated, all stretching being performed while the wire is at a temperature below its TTR. The wire remains dimensionally set while at this temperature, and it is installed in the mouth, with its extreme ends being soldered or bent as at 46 to affix it to the molar tubes 44. Then, the wire is heated, either by body temperature or an external heat source. This produces longitudinal shrinkage or contraction, tending to shorten the arch length and also tending to close the space between the teeth 36 and 38.

Preferably, the wire 48 is made relatively stiff by the substitution of cobalt for nickel on an atom-for-atom basis. This enables the wire to be used for leveling and uprighting the teeth in the manner described in connection with FIGS. 1 and 2. The property of mechanical memory is also useful in this context. For example, this archwire 48 may be formed into the desired final shape by a manufacturer at temperatures above the TTR. A temperature of about 1000° to 1200° F. for a few minutes is suitable for some Nitinol alloys. The desired final shape is usually parabolic, and it may include features such as offsets, insets, second order bends, bayonet bends, loops, curves and curves of spee, all being well known in the orthodontics field. Such an archwire while below its TTR is then attached by ligature wires to the tooth brackets, being bent and twisted as necessary for such attachment. The wire is then heated to a temperature above its TTR to activate the wire memory. The memory-produced internal stresses which tend to return the wire to its preset shape will impose forces on the teeth which urge them toward positions where the archwire will again be at its desired final shape. These forces may be compound forces which serve the multiple purposes of leveling, closing and uprighting the teeth.

In instances where the treatment does not require the closing of spaces between the teeth, prestretching of the archwire 48 is unnecessary and the mechanical memory of the preformed archwire will serve only to produce leveling and/or torquing of the teeth connected thereto.

In order further to control the positioning of teeth which are moved under the influence of a shrinkable archwire, a dual archwire system of the type shown on the upper jaw in FIG. 3 may be used. In this case, the upper archwire 50 is identical to the previously-described shrinkable archwire 48, both with respect to its metallurgical composition and the manner of installation. Of course, it tends to close the space between the two teeth 52 and 54.

The brackets used on the teeth of the upper jaw in FIG. 3 have dual slots which permit them to accommodate a second archwire 56. This archwire is not shrinkable and it may be made of unannealed Nitinol or conventional 18-8 stainless steel. Its function is to guide the teeth during the closing movement which occurs under the influence of the shrinking wire 50. The wire 56 may also be subjected to forces which cause it to level or torque the teeth. This technique, of course, provides for greater control of tooth movement during the closing phase of the orthodontic treatment.

Shrinkable wires may also be used to draw malposed teeth toward an ideal arch form as shown in FIGS. 4 and 5. In this instance, the wire is used in place of rubber band elastics now used in conventional practice. In FIGS. 4 and 5, a stiff archwire 58 is connected to banded-and-bracketed teeth 60-64. The teeth 60, 62 and 64 are substantially in the desired positions and their brackets are connected directly to the archwire 58 in a standard manner. The teeth 61 and 63, however, are malposed and require movement into alignment with the teeth 60, 62 and 64. This invention contemplates the use of a shrinkable elongated member, preferably a Nitinol ligature wire 65 which has been stretched while below its TTR, attached between the archwire 58 and the brackets of teeth 61 and 63 while below its TTR and then heated by body heat or an external heat source above its TTR. This produces longitudinal shrinkage of the wire 65 which will place it under tension and draw the teeth 61 and 63 toward the archwire 58. This shrinkable wire may have a diameter of about 0.010 inch and it is attached between the bracket and the archwire 58 in the manner illustrated best in FIG. 5. This ligature wire 65 first extends around the archwire 58 and then to the bracket where it passes along the slots in the bracket ears 66 as shown in FIG. 5. The wire 65 is then brought back to and around the archwire 58 where it is tied and twisted into a pigtail 68, the latter being bent back in the direction of the tooth to prevent irritation of surrounding mouth tissue. Other means may be used to affix the wire to the brackets or to itself, should the mechanical memory of the wire interfere with the illustrated knotand-pigtail securement. The mechanical memory of the wire which produces the shrinkage will place the ligature wires 65 under tension and create a force which draws the tooth 61 toward the rigid archwire 58 and toward a position of alignment with the teeth 60, 62 and 64. This technique may be a preliminary step leading to the use of archwires under flexure and/or tension as described in connection with the embodiments of FIGS. 1 and 2.

The Nitinol alloys preferably used in connection with the invention are near-stoichiometric alloys of nickel and titanium which, if expected to be subjected to torsional or flexural stresses, may have cobalt substituted to provide the composition of about $TiNi_{.935}Co_{.065}$. Such wires, when unannealed and in a single strand, have a higher elastic limit and a lower modulus of elasticity than an 18-8 stainless steel wire of the same cross-section. Even without cobalt, the Nitinol alloys are deformable by a martensitic shear mechanism when below a critical temperature (the TTR or transition temperature range), and possess a mechanical memory by returning to its original form when heated above this critical temperature.

The TTR of the wire should be below mouth temperature for all uses, and it preferably is above room temperature when the mechanical memory of the wire is to be utilized. In the latter case, a TTR of about 80°–90° F. is optimum. This permits the wire to be shaped while in its ductile condition without refrigeration, yet when raised to mouth temperature it tends to return toward its preset condition in order to exert the various disclosed types of tooth-moving forces.

When the wire is used to exert leveling or torquing forces on the teeth, it should be relatively stiff. Such stiffness is a property of the alloys including the transition element cobalt which is substituted for nickel on an atom-for-atom basis. Other suitable transition elements for the 55 Nitinol alloys are tantalum, niobium and copper; and, further experimentation may reveal that other atom-for-atom substitutes may be chromium, vanadium, iron, molybdenum, palladium and platinum.

One alloy of the type used in the practice of the invention is the subject of U.S. Pat. No. 3,351,463 which issued on Nov. 7, 1967 to Alexander G. Rozner and William J. Buehler. Other literature describing the processing and characteristics of suitable compositions is an article by Dr. William J. Buehler, the principal developer of the material, and William B. Cross entitled "55 Nitinol — Unique Alloy Wire" which appeared in the June, 1969, issue of Wire Journal. A description of the materials and certain of their properties also may be found in the brochure entitled "Nitinol Characterization Study" dated September, 1969. This document identified as N-69-36367 or NASA CR-1433 is available from the Clearing House For Scientific and Technical Information, Springfield, Va. 22151. All of these publications are incorporated herein by reference.

Earlier studies on the subject matter of this invention were reported by the inventor and his associates in the Journal of the American Dental Association (JADA) Volume 82, June, 1971, pages 1373 et seq; in The Angle Orthodontist, Volume 42, April 1972, pages 172–177; and in the American Journal of Orthodontics, May, 1973. These publications, together with the literature cited therein, are incorporated herein by reference.

Those skilled in the art will realize that only a few possible embodiments of the invention have been shown. While some aspects of the invention are directed to the specific use of Nitinol alloys, it will be appreciated that other compositions may exist or be developed which in some respects achieve substantially the same results in the same manner; and, further that there may be uses of the Nitinol alloys for providing tooth-moving forces other than those described herewithin. Therefore, it is emphasized that the invention is not in every respect limited to the particular embodiments shown herein but is defined by the claims which follow.

I claim:

1. A method of moving teeth by attaching a plurality of brackets to a plurality of teeth, subjecting the brackets and the teeth connected thereto to forces which urge them toward desired positions, the latter step being performed by subjecting a wire of a near-stoichiometric alloy of nickel and titanium to torsional forces and flexural forces before attaching it to the brackets, and non-rotatably attaching the wire to the brackets so that torsional restorative forces and flexural restorative forces act upon the brackets and teeth.

2. The method of claim 1 wherein only a single said wire is used.

3. The method of claim 1 wherein the alloy includes cobalt.

4. The method of claim 3 wherein the composition of the alloy is about $TiNi_{.935}Co_{.065}$.

5. The method of claim 1 wherein the wire is also subjected to bending stresses before attaching it to the brackets.

6. The method of claim 1 wherein the wire, when connected to the brackets, is subjected to said flexural forces by deflecting it at least 3 millimeters from its unstressed rest position.

7. The method of claim 6 wherein only a single said wire is used.

8. A method of moving teeth by attaching a plurality of brackets to a plurality of teeth, subjecting the brackets and the teeth connected thereto to forces which urge them toward desired positions, the latter step being performed by subjecting a wire to flexural forces and torsional forces before attaching it to the brackets, and non-rotatably attaching the wire to the brackets so that both torsional restorative forces and flexural restorative forces act upon the brackets and teeth, said wire being a single strand having a higher elastic limit and a lower elastic modulus than an 18-8 stainless steel wire having an identical cross-section.

9. The method of claim 8 wherein the wire when connected to the brackets is deflected at least 3 millimeters from its unstressed rest position.

10. The method of claim 8 wherein the wire is a near-stoichiometric alloy of nickel and titanium.

11. The method of claim 10 wherein the alloy includes a transition metal substituted for nickel on an atom-for-atom basis.

12. The method of claim 11 wherein the transition metal is cobalt.

13. The method of moving teeth comprising the steps of
attaching spaced-apart portions of an elongated member to a plurality of teeth, said elongated member having a preset form and a mechanical memory which returns it to its preset form in response to heating to a given temperature, said attaching step being performed at a temperature below said given temperature and while the archwire is in a deformed state which differs from its preset form heating the elongated member above said given temperature, thereby causing it to return toward its preset form to exert a moving force on the teeth.

14. The method of claim 13 wherein the elongated member in its deformed state is torsionally displaced from its preset form, whereby the heating step causes it to apply torsional forces on the teeth.

15. The method of claim 13 wherein the elongated member in its deformed state is flexurally displaced from its preset form, whereby the heating step causes it to apply flexural forces on the teeth.

16. The method of claim 13 wherein the elongated member in its deformed state is longitudinally elongated from its preset form, whereby the heating step longitudinally shrinks the wire to place it under tension.

17. The method of claim 16 wherein the elongated member is a ligature wire connected between one tooth and a rigid archwire spaced from the tooth, said archwire being connected to and supported by other said teeth.

18. The method of claim 16 wherein the elongated member is an archwire and the mentioned teeth are molars at the opposite ends of the archwire, whereby shrinkage of the archwire will create tensile forces which shorten the length of the arch by reducing the distance between said molars.

19. The method of claim 18 including the step of connecting a second archwire which is unshrinkable to a plurality of teeth molars to guide the closing movement of teeth produced by said shrinkable archwire.

* * * * *